| United States Patent [19] | [11] | 4,323,677 |
|---|---|---|
| D'Amico | [45] | Apr. 6, 1982 |

[54] N-AMIDES OF 2-BENZOTHIAZOLINONE

[75] Inventor: John J. D'Amico, Olivette, Mo.

[73] Assignee: Monsanto Company, St. Louis, Mo.

[21] Appl. No.: 51,483

[22] Filed: Jun. 25, 1979

Related U.S. Application Data

[63] Continuation of Ser. No. 861,476, Dec. 16, 1977, abandoned.

[51] Int. Cl.$^3$ .................. C07D 277/62; C07D 265/28
[52] U.S. Cl. .................................. 544/135; 544/368; 544/111; 71/90; 548/172
[58] Field of Search ............... 548/180; 544/368, 367, 544/111, 135; 71/90

[56] References Cited

U.S. PATENT DOCUMENTS

| 3,069,429 | 12/1962 | Gopson et al. | 260/304 |
|---|---|---|---|
| 3,661,921 | 5/1972 | Umio et al. | 260/304 |
| 3,755,327 | 8/1973 | Umio | 544/368 |
| 3,839,349 | 10/1974 | Wagner et al. | 260/304 |
| 3,993,468 | 11/1976 | D'Amico | 71/90 |
| 4,049,419 | 9/1977 | D'Amico | 71/76 |

FOREIGN PATENT DOCUMENTS 48-10182  3/1973  Japan.

Primary Examiner—Nicholas S. Rizzo
Attorney, Agent, or Firm—Stanley M. Tarter; Richard H. Shear; Howard C. Stanley

[57] ABSTRACT

N-amides of 2-benzothiazolinone have been found to be effective in regulating the growth of leguminous plants.

4 Claims, No Drawings

N-AMIDES OF 2-BENZOTHIAZOLINONE

This application is a continuation of Ser. No. 861,476 filed Dec. 16, 1977, now abandoned.

This invention relates to certain N-amides of 2-benzothiazolinone and their use as plant growth regulants. More specifically, the invention relates to amides having the formula

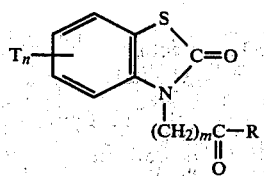

wherein T is trifluoromethyl and halo, n is 0 or 1; m is an integer from one to four; and R is selected from the group consisting of

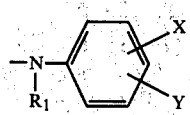

wherein X and Y are independently selected from the group consisting of hydrogen, halogen, lower alkyl and trifluoromethyl; $R_1$ is hydrogen or lower alkyl; and (II) heterocyclics selected from the group consisting of morpholino, 2,6-cis- and trans-dimethylmorpholino, cis- and trans-2,5-dimethylpyrrolidino, 3-azabicyclo (3.2.2) nonyl, and ethyl N-piperazinocarboxylate. Preferably, m is one.

The term "lower alkyl" as used herein is understood to mean those alkyl groups having from one to five carbon atoms inclusive. It is contemplated that the term alkyl includes primary, secondary and tertiary alkyls.

As a means of clarification, the heterocyclic moieties of the foregoing formula are defined below.

The term morpholino is understood to mean a radical having the structure

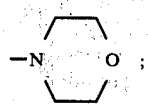

the term cis- and trans-2,6-dimethylmorpholino is understood to mean a mixture of radicals having the following structures

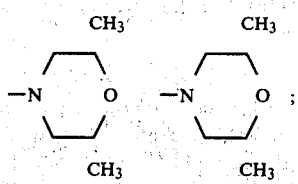

the term cis- and trans-2,5-dimethylpyrrolidino is understood to mean a mixture of radicals having the structure

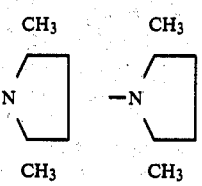

the term 3-azabicyclo (3.2.2) nonyl is understood to mean a radical having the formula

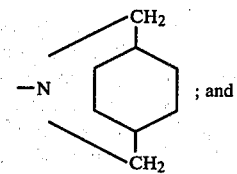

the term ethyl N-piperazinocarboxylate is understood to mean a radical having the formula

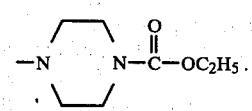

In accordance with the novel aspects of the present invention, N-amides of 2-benzothiazolinone of the foregoing formula have been found to be effective in regulating the growth of leguminous plants, such as soybeans. The compounds are especially effective in altering the leaf morphology of leguminous plants.

Leguminous plants have canopies that effectively inhibit sunlight from reaching the lower leaves. For example, only about 50% of a soybean plant's leaves intercept light from photosynthesis. Approximately 85% of the light is absorbed by the outer layer of leaves. Many researchers feel that by altering the morphology of the leaves such that the canopy is altered, light may fall more deeply into the canopy and yields could be increased. Weber, in Field Crop Abstracts, Vol. 21, No. 4, pages 313-317, states that "greater light penetration, resulting in greater amount of the [soybean] plant canopy having a light intensity above 150 f.c., generally led to higher seed yields". Johnson et al, in Crop Science, Vol. 9, pages 577-581, states that "adding light increased the yields of bottom, middle and top canopy positions of [soybean] plants 30, 20 and 2%, respectively". Thus, it would be highly beneficial if a method was found whereby the canopy of such plants could be altered such that a greater number of leaves could be illuminated.

As noted, the amides of the present invention are effective plant growth regulants. They are especially effective in altering the leaf morphology of leguminous plants.

The term "plant regulant" or "plant growth regulant", as employed in this application, connotes a material which serves to modify the normal sequential development of a treated plant to agricultural maturity. Such modification may result from the effect of material on the physiological processes of the plant or from the effect of said material on the morphology of the plant. It should additionally be recognized that modifications may also result from a combination or sequence of both physiological and morphological factors.

Modifying effects of a plant regulant are probably most readily observed as changes in the size, shape, color or texture of the treated plant or any of its parts. Similarly, changes in the quantity of the plant fruit or flowers are also quite apparent from simple, visual inspection. The above changes may be characterized as an acceleration or retardation of plant growth, such as increase or decrease in dry weight accumulation, stature reduction, leaf or canopy alteration, increased branching, terminal inhibition, increased flowering or fruit set.

Modifications in the normal sequential development of a treated plant to agricultural maturity may also be manifested by reduced transpiration or increased carbohydrate deposition or protein content.

It is to be understood that the regulation of plants in accordance with the instant invention does not include the total inhibition or the killing of such plants. Although phytotoxic amounts of the materials disclosed herein might be employed to exert a herbicidal (killing) action, it is contemplated herein to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amount will vary, not only with the material selected, but also with the modifying effect desired, the species of plant and its stage of development, the plant growth medium and whether a permanent or transitory effect is sought.

It is presently known that certain benzothiazyl compounds possess herbicidal activity. U.S. Pat. No. 3,069,429 discloses the use of derivatives of 4-halogeno-2-oxobenzothiazolin-3-ylacetic acid to kill weeds. U.S. Pat. No. 3,651,074 and 3,839,349 disclose the use of certain 2-oxo-3-benzothiazolines as a herbicide. None of these patents, however, disclose the use of the specific benzothiazolines used in accordance with the present invention to regulate the growth of plants. Further, none of these patents disclose the use of such benzothiazolines to alter the canopy of leguminous plants.

It is further known that certain benzothiazyl compounds possess plant growth regulating activity. U.S. Pat. No. 2,468,075 discloses the use of such compounds as abscission agents. Japanese Pat. No. 71/21378 discloses that such compounds possess plant growth regulating activity, but does not disclose any specific uses. Japanese Pat. No. 73/10182 discloses the use of benzothiazyl compounds as grafting agents for tree root growth. U.S. Pat. No. 3,661,921 discloses 2-oxo-3-benzothiazolineacetamides as anti-flammatory agents. U.S. Pat. No. 4,049,419 discloses the use of certain 2-oxo-3-benzothiazolineacetamides as plant growth regulants.

The prior art does not disclose, however, the heterocyclic amides of 2-benzothiazolinone of the foregoing formula nor does the prior art disclose the use of the amides of the foregoing formula as a plant growth regulant for leguminous plants.

Generally, the amides of the invention are prepared by reaction of the appropriate acid chloride of 2-benzothiazolinone with the appropriate amine. Said acid chlorides may be prepared in accordance with my copending application Ser. No. 735,658 filed Oct. 26, 1976 wherein the preparation of 2-oxo-3-benzothiazolineacetyl chloride is disclosed. That application discloses N-substituted 2-benzothiazolinones including certain N-acetamides of 2-benzothiazolinone.

Alternatively, amides of the foregoing formula in which R is

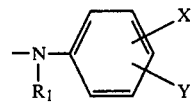

may be prepared by reacting 2-benzothiazolol with the appropriate chloroalkylanilide.

To illustrate the method for preparing the compounds of the invention, the following examples are presented. Said examples are meant to be for illustration only and are not included as a limitation on the scope of the invention.

EXAMPLE 1

To a stirred slurry containing 15.9 grams (0.07 mole) of 2-oxo-3-benzothiazolineacetyl chloride in 200 ml of heptane, 0.2 moles of cis- and trans-2,5-dimethylpyrrolidine is added in one portion. The stirred reaction mixture is heated at reflux for six hours and held at 25°–30° C. for about 18 hours. After addition of 800 ml of water, stirring is continued at 25°–30° C. for 30 minutes. The solid is collected by filtration, washed with water until neutral to litmus and air-dried at 25°–30° C. Analytical data is summarized in Table I, below.

EXAMPLES 2–16

The procedure of Example 1 is repeated utilizing in lieu of cis- and trans-2,5-dimethylpyrrolidine the following amines.
  Example 2—3-azabicyclo (3.2.2) nonane
  Example 3—ethyl N-piperazinecarboxylate
  Example 4—m-trifluoromethylaniline
  Example 5—m-chloroaniline
  Example 6—o-chloroaniline
  Example 7—o-fluoroaniline
  Example 8—p-fluoroaniline
  Example 9—2-chloro-5-trifluoromethylaniline
  Example 10—cis- and trans-2,6-dimethylmorpholine
  Example 11—2-trifluoromethyl-4-chloroaniline
  Example 12—3,5-ditrifluoromethylaniline
  Example 13—3-trifluoromethyl-4-chloroaniline
  Example 14—m-fluoroaniline
  Example 15—p-chloroaniline
  Example 16—aniline

EXAMPLE 17

The procedure of Example 1 is repeated utilizing 5-chloro-2-oxo-3-benzothiazolineactyl chloride in lieu of 2-oxo-3-benzothiazolineactyl chloride and m-trifluoromethylaniline in lieu of cis- and trans-2,5-dimethylpyrrolidine.

EXAMPLE 18

To a stirred solution containing 15.1 grams (0.1 mole) of 2-benzothiazolol, 6.6 grams (0.1 mole) of 85% potassium hydroxide, 200 ml of acetone and 10 ml of water, 0.1 mole of 2-chloro-N-isopropylacetanilide is added in one portion. The stirred reaction mixture is heated at reflux for six hours and at 25°–30° C. for 18 hours. After the addition of 800 ml of water, stirring is continued for 30 minutes. The solid is collected by filtration, washed with water until the washings are neutral to litmus and air-dried at 25°–30° C. The product, m.p. 165°–166° C., is obtained in 89% yield. After recrystallization from isopropyl alcohol, it melted at 166°–167° C.

EXAMPLE 19

To a stirred solution containing 8.4 grams (0.055 mole) of 2-benzothiazolol, 3.7 grams (0.055 mole) of 85% potassium hydroxide, 100 ml of DMF and 10 ml of water, 12 grams (0.05 mole) of 2-chloro-2′,6′-diethyl-N-methylacetanilide is added in one portion. The stirred reaction mixture is heated at 80°–90° C. for 24 hours. After cooling to 25° C., 800 ml of water is added and stirring continued at 25°–30° C. for 30 minutes. The solid is collected by filtration, washed with water until the washings are neutral to litmus and air-dried at 25°–30° C. The product, m.p. 161°–162° C., is obtained in 93% yield. After recrystallization from isopropyl alcohol, it melted at 163°–164° C.

Analytical data for the compounds of Examples 1–19 is summarized in Table I, below.

TABLE I

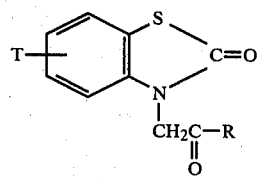

| Example Number | T | R | m.p. °C. | Percent Yield | Percent C Calc'd. | Found | Percent H Calc'd. | Found | Percent N Calc'd. | Found | Percent S Calc'd. | Found |
|---|---|---|---|---|---|---|---|---|---|---|---|---|
| 1 | H | —N(CH$_3$)$_2$ | 167–8[a] | 74 | 62.04 | 61.94 | 6.25 | 6.30 | 9.65 | 9.71 | 11.04 | 11.07 |
| 2 | H | —N(CH$_2$)$_4$CH$_2$ (piperidinyl) | 198–9[b] | 81 | 64.53 | 64.52 | 6.37 | 6.41 | 8.85 | 8.88 | 10.13 | 10.08 |
| 3 | H | —N(piperazinyl)NCOC$_2$H$_5$ | 165–6[c] | 57 | 55.00 | 55.19 | 5.48 | 5.53 | 12.03 | 12.00 | 9.18 | 9.11 |
| 4 | H | —NH–C$_6$H$_4$–CF$_3$ | 241–2 | 93 | 54.54 | 54.57 | 3.15 | 3.16 | 7.95 | 8.02 | 9.10 | 9.12 |
| 5 | H | —NH–C$_6$H$_4$–Cl | 242–3 | 98 | 56.52 | 56.40 | 3.48 | 3.49 | 8.79 | 8.81 | 10.06 | 10.16 |
| 6 | H | —NH–C$_6$H$_4$–Cl | 218–9 | 90 | 56.52 | 56.49 | 3.48 | 3.49 | 8.79 | 8.78 | 10.06 | 10.11 |
| 7 | H | —NH–C$_6$H$_4$–F | 211–2 | 95 | 59.59 | 59.40 | 3.67 | 3.71 | 9.27 | 9.21 | 10.61 | 10.54 |
| 8 | H | —NH–C$_6$H$_4$–F | 215–6 | 90 | 59.59 | 59.71 | 3.67 | 3.71 | 9.27 | 9.32 | 10.61 | 10.63 |
| 9 | H | —NH–C$_6$H$_3$(Cl)(CF$_3$) | 212–3 | 89 | 49.69 | 50.18 | 2.61 | 2.77 | 7.24 | 7.22 | — | — |
| 10 | H | —N(CH(CH$_3$)CH$_2$)$_2$O (morpholinyl dimethyl) | 187–8[b] | 75 | 58.80 | 58.61 | 5.92 | 5.98 | 9.14 | 9.07 | 10.47 | 10.52 |
| 11 | H | —NH–C$_6$H$_3$(Cl)(CF$_3$) | 251–2[b] | 92 | 49.69 | 49.55 | 2.61 | 2.64 | 7.24 | 7.15 | 8.28 | 8.39 |

TABLE I-continued

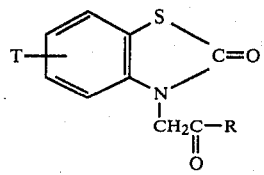

| Example Number | T | R | m.p. °C. | Percent Yield | Percent C Calc'd. | Found | Percent H Calc'd. | Found | Percent N Calc'd. | Found | Percent S Calc'd. | Found |
|---|---|---|---|---|---|---|---|---|---|---|---|---|
| 12 | H | —NH—C$_6$H$_3$(CF$_3$)$_2$ | 272–3[c] | 82 | 48.58 | 48.67 | 2.40 | 2.45 | 6.66 | 6.65 | 7.63 | 7.73 |
| 13 | H | —NH—C$_6$H$_3$(CF$_3$)Cl | 260–1[c] | 93 | 49.69 | 49.72 | 2.61 | 2.65 | 7.24 | 7.31 | 8.28 | 8.39 |
| 14 | H | —NH—C$_6$H$_4$F | 238–9[c] | 95 | 59.59 | 59.50 | 3.67 | 3.68 | 9.27 | 9.28 | 10.61 | 10.69 |
| 15 | H | —NH—C$_6$H$_4$Cl | 247–8[d] | 94 | 56.52 | 56.72 | 3.48 | 3.74 | 8.79 | 9.04 | 10.06 | 9.88 |
| 16 | H | —NHC$_6$H$_5$ | 216–7[e] | 77 | 63.36 | 63.28 | 4.25 | 4.27 | 9.85 | 9.87 | 11.28 | 11.36 |
| 17 | 5-Cl | —NH—C$_6$H$_4$CF$_3$ | 241–2[c] | 94 | 49.69 | 49.64 | 2.61 | 2.60 | 7.24 | 7.27 | 8.29 | 8.33 |
| 18 | H | —N(CH(CH$_3$)$_2$)—C$_6$H$_5$ | 166–7[a] | 89 | 66.23 | 66.17 | 5.56 | 5.59 | 8.58 | 8.63 | 9.82 | 9.89 |
| 19 | H | —N(CH$_3$)—C$_6$H$_4$(C$_2$H$_5$)(C$_2$H$_5$) | 163–4[a] | 93 | 68.82 | 68.59 | 6.05 | 6.14 | 7.64 | 7.66 | 8.75 | 8.90 |

[a]Recrystallization from isopropyl alcohol.
[b]Recrystallization from toluene.
[c]Recrystallization from ethyl acetate.
[d]Recrystallization from DMF.
[e]Recrystallization from methyl alcohol.

In accordance with the novel aspects of the present invention, the amides of the foregoing formula are used as the active ingredient in compositions that are useful as plant growth regulants. In practicing the plant growth regulating methods of this invention, the active ingredient can be used alone or in combination with a material referred to in the art as an adjuvant in liquid or solid form. The plant growth regulating compositions of this invention are prepared by admixing the active ingredient with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent, or emulsifying agent or any suitable combination of these.

When applying the active ingredient to leguminous plants, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful in applying the active ingredient to leguminous plants include, for example, Stoddard solvent, acetone, alcohols, glycols, ethyl acetate, benzene and the like. Such leguminous plant growth regulating compositions, particularly liquids and wettable powders, usually contain as a conditioning agent one or more surface-active agents in amounts sufficient to render a given composition readily dispersible in water or in oil. By the term "surface-active agent" it is understood that wetting agents, dispersing agents, suspending agents and emulsifying agents are included therein. Such surface-active agents are well known and reference is made to U.S. Pat. No. 2,547,724, columns 3 and 4, for detailed examples of the same.

Compositions of this invention generally contain from about 5 to 95 parts active ingredient, about 1 to 50 parts surface-active agent and about 4 to 94 parts solvent, all parts being by weight based on the total weight of the composition.

Desirable modification of leguminous plants may be achieved by applying the above-described plant regulants to the plant locus. The term "plant locus" is understood herein to include the plant growing medium, such as the soil, as well as the seeds, emerging seedlings, roots, stems, leaves, flowers, fruits or other plant parts.

The application of liquid and particulate solid compositions of the active ingredient can be carried out by conventional techniques utilizing, for example, spreaders, power dusters, boom and hand sprayers and spray dusters. The compositions can also be applied from airplanes as a dust or spray. If desired, application of the compositions of the invention to leguminous plants can be accomplished by incorporating the compositions in the soil or other media in the area where modification of the plants is desired.

To illustrate the variety of regulatory responses observed, the compounds of the invention were tested in accordance with the following procedure.

A number of soybean plants are grown from seeds in plastic pots in the greenhouse for a period of one week at which time the plants are thinned to one plant per pot. When the second trifoliate leaf is fully expanded, the plants are treated with a solution of the active ingredient in acetone and water. Aqueous Tween 20 is used as a surfactant.

When the fifth trifoliate leaf of the control is fully expanded, the treated plants are compared with the nontreated control plants and the observations recorded.

Table II, below, summarizes those results and observations.

TABLE II

| Compound of Example No. | Rate (kg/ha) | Observations |
|---|---|---|
| 1 | 2.8 | Leaf alteration, altered canopy. |
| | 0.56 | No response. |
| | 0.112 | No response. |
| 2 | 2.8 | Leaf alteration. |
| | 0.56 | Leaf alteration. |
| | 0.112 | No response. |
| 3 | 2.8 | Leaf distortion of new growth, leaf alteration of new growth, leaf inihibition, stature reduction, altered canopy. |
| | 0.56 | Leaf distortion of new growth, leaf alteration of new growth, altered canopy, chlorosis. |
| | 0.112 | Leaf alteration. |
| 4 | 2.8 | Increase in dry weight accumulation. |
| | 0.56 | No response. |
| | 0.112 | Leaf alteration. |
| 5 | 2.8 | Leaf alteration of existing growth, decrease in dry weight accumulation. |
| | 0.56 | Leaf alteration, decrease in dry weight accumulation. |
| | 0.112 | Decrease in dry weight accumulation. |
| 6 | 2.8 | Leaf alteration of new growth, leaf inhibition, altered canopy. |
| | 0.56 | Leaf alteration of new growth, leaf inhibition, altered canopy. |
| | 0.112 | Leaf alteration of new growth, leaf inhibition, altered canopy. |
| 7 | 2.8 | Leaf alteration of new growth, leaf inhibition, altered canopy. |
| | 0.56 | Leaf alteration of new growth, leaf inhibition. |
| | 0.112 | Leaf alteration of new growth. |
| 8 | 2.8 | Leaf alteration of existing growth, leaf alteration of new growth, leaf inhibition, altered canopy. |
| | 0.56 | Leaf alteration of new growth. |
| | 0.112 | No response. |
| 18 | 2.8 | No response. |
| | 0.56 | No response. |
| | 0.112 | Increase in dry weight accumulation. |

The above data illustrates that the compounds of the invention are rather effective in altering the leaf morphology of soybean plants. Such alteration may lead to enhanced photosynthesis.

In selecting the appropriate non-toxic rate of application of the active ingredient to leguminous plants, it will be recognized that precise rates will also be dependent upon the mode of application, such as soil incorporation, band application, pre-plant seed treatment, result desired and various other factors known to those skilled in the art. In applications to the soil habitat of germinant seeds, emerging seedlings, and established vegetation for the regulation of plant growth, the active ingredients are applied in amounts of from about 0.05 to about 20 pounds per acre or more (0.056 to 22.4 kilos/hectare). Foliar application is particularly advantageous and is preferred, especially at rates from about 0.1 to about 5.0 pounds per acre (0.112 to 5.6 kilos/hectare).

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. An N-amide of 2-benzothiazolinone characterized by the formula

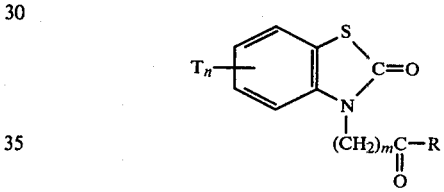

wherein T is trifluoromethyl and halo, n is 0 or 1; m is an integer from one to four; and R is selected from the group consisting of heterocyclics selected from the group consisting of cis- and trans-2,6-dimethylmorpholino, cis- and trans-2,5-dimethylpyrrolidino, 3-azabicyclo (3.2.2) nonyl, and ethyl N-piperazinocarboxylate.

2. A compound according to claim 1 wherein R is selected from the group consisting of 3-azabicyclo (3.2.2) nonyl and ethyl N-piperazinocarboxylate.

3. A compound according to claim 1 wherein R is selected from the group consisting of cis- and trans-2,6-dimethylmorpholino and ethyl N-piperazinocarboxylate.

4. A compound according to claim 1 wherein m is one.

* * * * *